United States Patent [19]

Lohr

[11] Patent Number: 4,586,818

[45] Date of Patent: May 6, 1986

[54] MEASURING STATION FOR A PHOTOMETER

[75] Inventor: Willy Lohr, Wildbad, Fed. Rep. of Germany

[73] Assignee: Laboratorium Prof. Dr. Rudolf Berthold, Wildbad, Fed. Rep. of Germany

[21] Appl. No.: 545,501

[22] Filed: Oct. 26, 1983

[30] Foreign Application Priority Data

Oct. 27, 1982 [DE] Fed. Rep. of Germany ... 8230199[U]

[51] Int. Cl.⁴ .................. G01N 21/00; G01N 21/01
[52] U.S. Cl. .................................. 356/244; 356/246
[58] Field of Search ............................... 356/244, 246

[56] References Cited

U.S. PATENT DOCUMENTS

| | | | |
|---|---|---|---|
| 3,588,259 | 6/1971 | Harvey | 356/244 |
| 3,881,826 | 5/1975 | De Leeuw | 356/246 |
| 3,881,872 | 5/1975 | Naono | 422/64 |
| 4,121,907 | 10/1978 | Roque | 356/246 |
| 4,240,749 | 12/1980 | Retzer | 356/246 |
| 4,390,274 | 6/1983 | Berthold et al. | 356/436 X |
| 4,424,279 | 1/1984 | Bohn et al. | 210/927 X |

FOREIGN PATENT DOCUMENTS

| | | |
|---|---|---|
| 1101902 | 2/1968 | United Kingdom . |
| 1167204 | 10/1969 | United Kingdom . |
| 1230031 | 4/1971 | United Kingdom . |
| 1331072 | 9/1973 | United Kingdom . |
| 1413267 | 11/1975 | United Kingdom . |
| 1466779 | 3/1977 | United Kingdom . |
| 1546863 | 5/1979 | United Kingdom . |

Primary Examiner—John E. Kittle
Assistant Examiner—Mukund J. Sham
Attorney, Agent, or Firm—Spencer & Frank

[57] ABSTRACT

A measuring station for a photometer has an aperture which connects a measuring chamber and the environment and through which a sample vessel can be introduced into the measuring chamber and/or removed from the measuring chamber. The sample vessel is raised and lowered by a plunger which is adapted to seal against the aperture by means of a sealing element. The sealing element has a first position in which its periphery circumscribes a smaller area than the internal clear cross-section of the aperture, to permit the sample vessel to be lifted into the chamber. The sealing element can then be expanded radially into sealing engagement with the aperture to seal the plunger to the walls of the aperture to prevent ingress of light.

19 Claims, 2 Drawing Figures

MEASURING STATION FOR A PHOTOMETER

BACKGROUND OF THE INVENTION

The present invention relates to a measuring station for a photometer. The term "photometer" refers to light measuring apparatus in general and includes photometers using light absorption, light diffusion, liquid scintillation, luminescence or the like. Photometers using luminescence are sometimes referred to as luminometers.

One known measuring station for a photometer has a hollow measuring chamber into which a sample is introduced through an aperture by means of a plunger. Such a measuring chamber may be used, for example, for the uses described in German Offenlegungsschrift No. 29 01 919, and corresponding U.S. Pat. No. 4,390,274.

In measuring stations in which a plunger lifts the sample or a sample vessel containing a sample to be measured into the measuring chamber, the plunger has to have a smaller cross section than the aperture through which the sample or sample vessel passes into the measuring chamber. This raises the problem of sealing the plunger to the walls of the aperture in order to prevent light ingress into the measuring chamber which would otherwise ruin the measurement. It would be possible to seal the plunger to the measuring chamber by means of a sealing element in the form of a multiple-leaf diaphragm located in the aperture, the diaphragm closing around the plunger when the sample has been introduced into the measuring chamber. However, such an arrangement would be complex and expensive.

SUMMARY OF THE INVENTION

The present invention seeks to solve the problem of sealing the plunger to the aperture by providing a sealing element on the plunger. The sealing element is expandable between a first position, in which its area is less than the minimum cross sectional area of the aperture and a second position. The plunger introduces the sample into the measuring chamber, then the sealing element is expanded to the second position to seal the plunger to the walls of the aperture. The plunger preferably raises the sample into the measuring chamber, but arrangements are also possible in which the sample is lowered into the measuring chamber by the plunger.

It is preferable that the sealing element is adapted to return automatically to the first position from the second position. This may be achieved, for example, by making the sealing element of resilient material. It has been found that the elasticity of a normal O-ring is sufficient to provide the necessary restoring force to return to the first position. In this way it is necessary to provide only means for expanding the sealing element, which expansion may be relatively small, e.g. 10% of its radius when in the first position.

The expansion of the sealing element may be achieved by providing two expander elements on the plunger, the sealing element being held between the expander elements, which are movable axially relative to each other to expand the sealing element. The relative movement of the expander elements is preferably achieved by the cooperation of one of the expander elements with an axially displacable actuating element via a spring element. This ensures relatively gentle transmission of the expanding force from the actuating element to the expander element.

Reliable expansion of the sealing element, and reliable sealing of the sealing element both to the walls of the aperture and to the plunger may be achieved by providing a sealing surface on the plunger, e.g. on one of the expander elements, the radial extent of which surface increases axially along the plunger. The sealing element is thus held between that surface and another sealing surface on, for example, the other expander element. If the sealing element is a resilient O-ring, it may be deformed from an approximately circular cross-section to a form with one surface abutting on the surface bonding the aperture and two other surfaces abutting the sealing surfaces on the expander elements.

A holder may be provided adjacent the measuring chamber with a bore for holding a sample vessel prior to its introduction into the measuring chamber. The cross-sectional area of the bore is such that it is less than the area circumscribed by the periphery of the sealing element when the latter is in its first position. This permits the plunger to move through the bore. The holder preferably has an internal step in the bore for supporting the sample vessel. It is sometimes necessary that when the sample vessel is returned to the holder, it is not put back on the internal step. One reason for this is to enable the sample to be decanted. Therefor, an inwardly directed projection may be provided in the bore above the internal step. The projection engages frictionally the sample vessel to hold the latter in the bore.

BRIEF DESCRIPTION OF THE DRAWINGS

An embodiment of the present invention will now be described in detail, by way of example, with reference to the accompanying drawings, in which.

DETAILED DESCRIPTION OF THE PREFERRED EMBODIMENT

Figure 1:
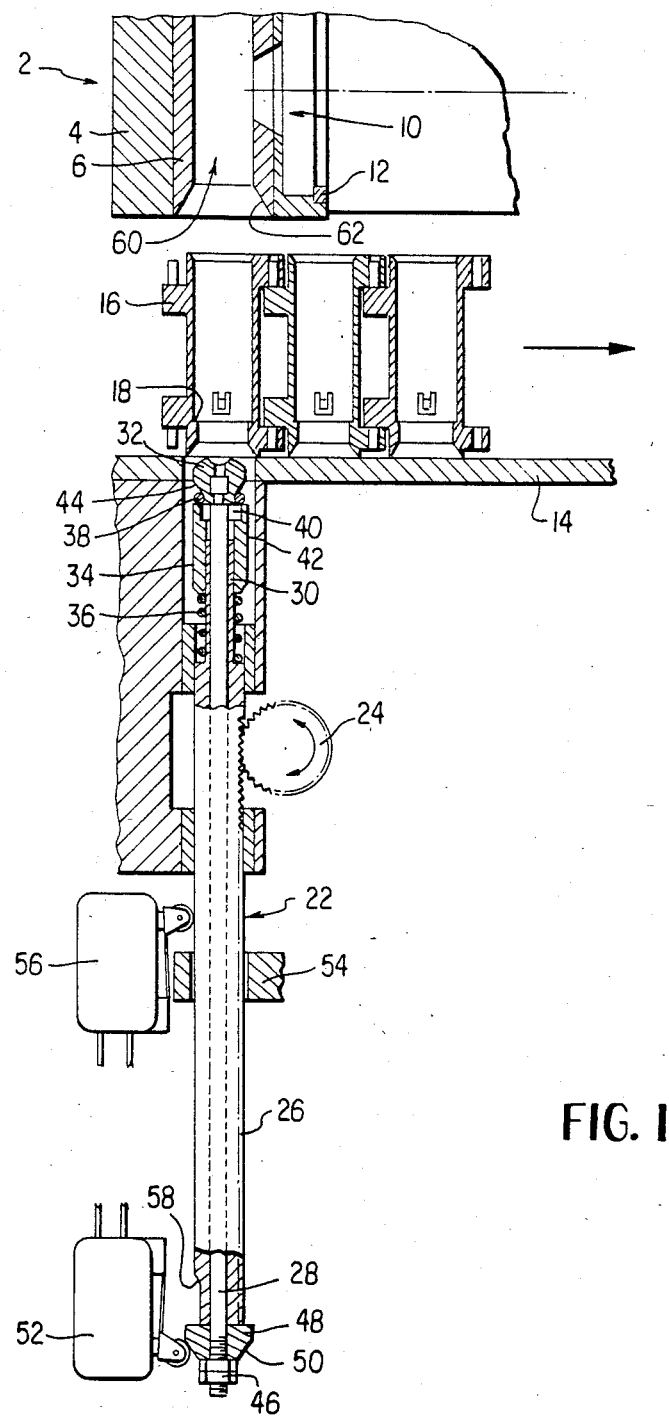
FIG. 1 shows a vertical section through a measuring station according to the present invention with the plunger in a position withdrawn from the measuring chamber.

A measuring station 2 according to the present invention comprises a housing block 4 in which a sheath 6 is inserted vertically. The inner surface of this sheath 6 is cylindrical and corresponds, with a small clearance, to the outer diameter of a test tube 8 serving as a sample vessel. The sheath 6 may be interchangeable in the housing block 4, with other sheaths of different internal diameter to allow the block to be adapted to test tubes 8 of various outer diameters. The sheath 6 may be durably sealed in a lightproof manner at its axially uppermost end in a manner not shown. The sheath 6 and housing block 4 are provided on one side with a window 10 to which a photometric measuring apparatus can be attached in a lightproof manner and sealed securely to the housing block 4 by means of a sealing ring 12.

A measuring chamber is thus formed by the cylindrical interior space 13 within the sheath 6.

Figure 2:
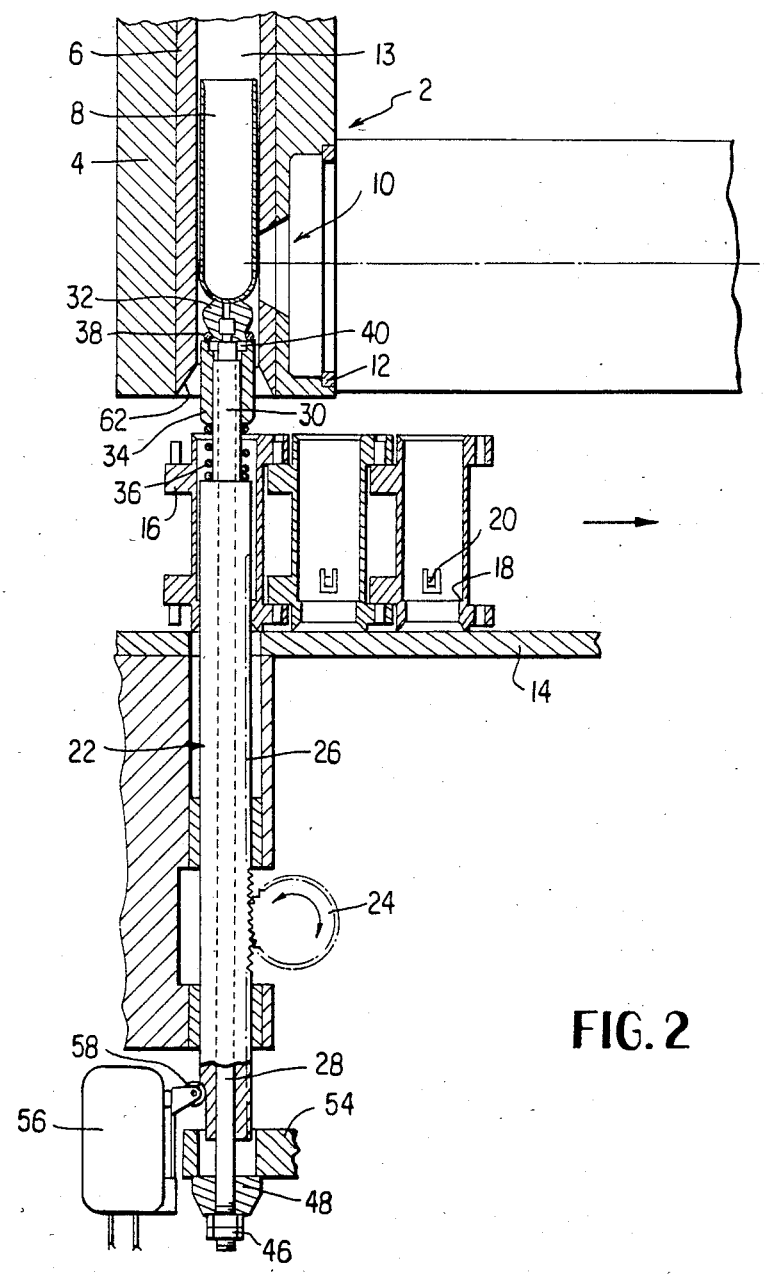
FIG. 2 shows a similar view but with the plunger raised and a sample vessel situated within the measuring chamber, the plunger being sealed to the aperture of the measuring chamber.

The measuring station 2 is arranged above a working table 14 on which holders 16 engaging in one another like chain links can be guided stepwise below the measuring station 2. Sample vessels 8 are placed in the holders and each one supported on a corresponding internal rim or shoulder 18 of the holders 16, each shoulder 18 being in the form of an encircling ring. Stepwise movement of the holders 16 causes each sample vessel 8 to arrive sequentially below the measuring chamber. An internal projection 20 (FIG. 2), which is arranged above the shoulder 18 and is for example of puntiform type, abuts on a peripheral surface of the sample vessel 8, the friction between the projection 20 and the vessel 8 retaining the vessel 8 in position. When the sample vessel 8 is returned to the holder 16 from the measuring chamber, such a sample vessel 8 can rest freely on top of the internal projection 20, so that decanting of the sample if no longer required is made easier.

A plunger 22 is displaceable axially upwardly and downwardly in the working table 14 by means of a pinion 24. The pinion 24 engages a cylindrical toothed rack of an actuating element in the form of an outer plunger 26, the tooth system being constructed in the form of successive peripheral indentations provided axially along the outer plunger 26. An inner plunger 28 is axially displaceable relatively to the outer plunger 26.

The inner plunger is in the form of a cylindrical rod with an extension 30 which projects upwards from the outer plunger 26. The inner plunger 28 has a head 32 secured to its upper end. The end face of the head 32 forms a bearing surface substantially complementary with the base of the sample vessel 8, and is so dimensioned that it will fit through the holder 16 even in the region of the internal rim or shoulder 18 of the holder 16. Below the head 32 a sleeve 34 is guided in axially displaceable manner on the extension 30. The radial extent of the sleeve 34 corresponds to the maximum radial extent of the head 32 and the sleeve 34 is biassed in the direction of the head 32 by a helical mechanical compression spring 36, which is provided around the extension 30 between the sleeve 34 and that end of the outer plunger 26 which is directed towards the sleeve 34.

A sealing element 38 in the form of an O-ring is mounted between the head 32 and the sleeve 34, and FIG. 1 shows the first or relaxed condition. As shown in FIG. 1 the radially inward surface of the sealing element 38 abuts a cylindrical surface 40 of the head. Below the sealing element 38 is a sleeve-form extension 42 of the sleeve 34, whereas above the element 38 is an upwardly widening conical sealing surface 44 on the head 32. The extension 42 and the sealing surface 40 seal the sleeve 34 and the head 32, respectively, to the sealing element 38. Alternatively, the cylindrical surface 40 and the end face of the sleeve-like extension 42, can be replaced by a conically downwardly extending sealing surface on the sleeve 34 and an extension on the head 32. The first position of the sealing element 38 is adjustable by appropriate adjustment of nuts 46 at the lower end of the inner plunger 28.

An abutment ring 48 is situated directly above the nuts 36 on the inner plunger 28. This ring 48 has a double function. As shown in FIG. 1, it has a conically downwardly tapering switching surface 50 which cooperates with a first limit switch 52 which determines the lower operating position of the plunger. Also, when the inner plunger 28 has been raised to its upper position shown in FIG. 2 the ring 48 acts as an abutment against a limit plate 54 of the working table and so defines the operating position of the sample vessel 8. The limit plate 54 may be constructed as a guide for the plunger 22. When the inner plunger 28 has reached its upper position, the outer plunger 26 can be displaced further upwards by means of the pinion 24, until a second limit switch 56 engages a narrowed switching surface 58 on the outer plunger 26. This ends the upward movement of the outer plunger 26.

When the outer plunger 26 moves upward relative to the inner plunger 28, the sleeve 34 is also pushed upwards, its movement being resisted by the spring element 36, and the sealing element 38 is expanded, the sleeve 34 and the conical surface 44 of the head 32 co-operating to cause the sealing element 38 to expand. The sleeve 34 and the conical surface 44 of the head 32 then form expander elements for the sealing element 38. The sealing element 38 comes to abut on the cylindrical inner surface of the sheath 6. The aperture 60 of the measuring chamber is described by the internal clear cylindrical cross-section thereof, which widens conically outwards at the lower inlet side, as shown at 62.

In the first or relaxed position illustrated in FIG. 1, the sealing element 38 has a radial extent such that it can pass without difficulty through the narrowest regions of the holder 16. In the operating position illustrated in FIG. 2, the sealing element 38 is opened out or expanded until it abuts on the cylindrical inner surface of the sheath 6 and thus seals the aperture 60, whereby the measuring chamber is closed in lightproof manner in the region of the aperture intended for the introduction and removal of the sample vessel 8. The compression spring 36 allows the O-ring sealing element 38 to be expanded uniformly and carefully, and also provides a greater tolerance for the switchoff point of the second limit switch 56. This also ensures that the sealing element 38 is not moved vertically in the expanding operation, allowing the sealing arrangement and thus the entire measuring station 2 also to have a particularly long service life.

The term "measuring station for a photometer" used herein refers not only to photometers in the form of light-absorbing apparatus, but also to light measuring apparatus in general, whether using simple light diffusion, luminescence, or the like. Such photometers are sometimes also referred to as luminometers.

What is claimed is:

1. A measuring station for a photometer comprising:
   a hollow measuring chamber, said hollow measuring chamber having at least one aperture therein, said at least one aperture connecting the interior of said hollow measuring chamber with the exterior thereof;
   a plunger for introducing a sample into said hollow measuring chamber through said at least one aperture; and
   a sealing element on said plunger, said sealing element having a first position in which the area circumscribed by the periphery of said sealing element is less than the minimum cross-sectional area of said aperture, and being expandable radially relative to said plunger to a second position; and
   wherein expansion of said sealing element when said sample is introduced into said hollow measuring chamber seals said plunger to said measuring chamber in said aperture.

2. A measuring station according to claim 1, wherein said plunger is movable generally upwards for raising a sample vessel containing said sample into said hollow measuring chamber.

3. A measuring station according to claim 1, wherein the extent of the radial expansion of said sealing element from said first position to said second position is angularly invariable.

4. A measuring station according to claim 1, wherein said sealing element is adapted to return automatically to said first position from said second position.

5. A measuring station according to claim 1, wherein said sealing element is formed from elastomeric material.

6. A measuring station according to claim 1, wherein said sealing element is an O-ring.

7. A measuring station according to claim 1, wherein said measuring chamber has a sealing surface bounding said aperture, which sealing surface is axially parallel to said sealing element on said plunger.

8. A measuring station according to claim 1, wherein said plunger has two opposing sealing surfaces, and said sealing element is held axially and radially between said opposing sealing surfaces when said sealing element is in said second position.

9. A measuring station according to claim 8, wherein the radial extent of at least one of said opposing sealing surfaces increases axially along said plunger.

10. A measuring station according to claim 1 further comprising a holder for a sample vessel for said sample, said holder having a bore therethrough, an internal step being located in said bore for supporting a sample vessel for said sample prior to the introduction of said sample into said hollow measuring chamber by said plunger, the cross-sectional area of said bore being greater than the area circumscribed by the periphery of said sealing element when said sealing element is in said first position, whereby said plunger is movable into said bore when said sealing element is in said first position.

11. A measuring station according to claim 10, wherein said holder has an inwardly directed projection in said bore above said internal step, said inwardly directed projection engaging frictionally a surface of said sample vessel when said sample vessel is supported in said bore.

12. A measuring station according to claim 1, wherein said sealing element is expansible by approximately 10% of its radius when it expands from said first position to said second position.

13. A measuring station according to claim 1, wherein said plunger has two expander elements, said expander elements being adjustable axially relative to one another, said sealing element being held between said expander elements.

14. A measuring station according to claim 13, including an axially displaceable actuating element and a spring element, said actuating element co-operating with one of said expander elements by way of said spring element.

15. A measuring station according to claim 14, wherein said actuating element forms a part of said plunger, said plunger further including:
an inner plunger on which said spring element is mounted, movement of said actuating element relative to said inner plunger being transmitted to said one of said expander elements by said spring element; and
a head on said inner plunger, the other of said expander elements being formed by a part of said head.

16. A measuring station according to claim 15, wherein said actuating element has a toothed rack for engagement with a drive pinion for moving said actuating element.

17. A measuring station according to claim 16, wherein said toothed rack is formed by a row of indentations in said actuating element, said indentations provided axially along the outer plunger.

18. A measuring station according to claim 15 having means for limiting axial movement of said inner plunger when said sample has been introduced into said hollow measuring chamber by said plunger.

19. A measuring station according to claim 1, wherein the radial extent of said sealing element in said first position is adjustable.

* * * * *